Oct. 3, 1944. M. R. JACOBUS Plant Pat. 643
ROSE PLANT
Filed April 7, 1944
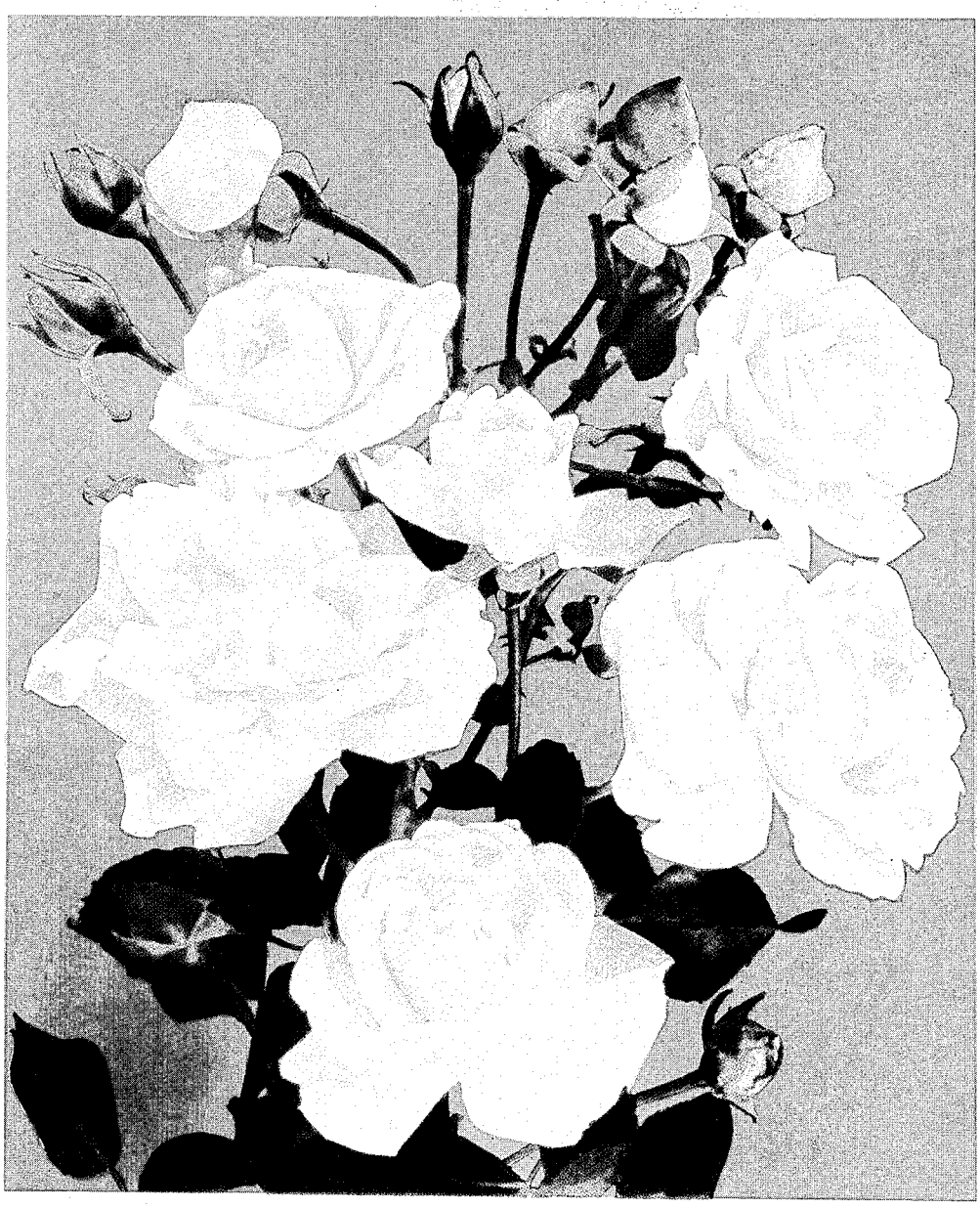
INVENTOR
Martin R. Jacobus
By Orville M. Kile
Plant Pat. Agt.

Patented Oct. 3, 1944

Plant Pat. 643

UNITED STATES PATENT OFFICE

643

ROSE PLANT

Martin R. Jacobus, Ridgefield, N. J., assignor to Bobbink & Atkins, East Rutherford, N. J., a corporation of New Jersey Application April 7, 1944, Serial No. 530,021

1 Claim. (Cl. 47—61)

My present invention relates to a new and distinct variety of climbing rose plant, the successful result of definite breeding efforts to produce a hardy, everblooming, fragrant, large-flowered climbing rose variety characterized by a color or combination of colors never before seen in any class of climbing rose.

My new rose variety was produced by crossing the New Dawn everblooming climbing rose and the everblooming hybrid tea Senora Gari. The female or seed parent was New Dawn and the male or pollen parent was Senora Gari.

The climbing habit of growth of this new variety is practically the same as that of New Dawn, the plant at the end of several years attaining a height of approximately eight or nine feet and an equal spread. It has proved to be equally as hardy as New Dawn. These two features of hardiness and climbing growth were what I desired to be transmitted to the new variety, although other desirable qualities also resulted.

The very pleasing spicy and penetrating fragrance is extremely important particularly as this fragrance comes from the blooms allowed to open both outdoors and indoors. The fragrance becomes more pronounced and lasting in the later stages of bloom development, which is also a most unusual characteristic of this new variety.

Because of their size and long lasting qualities, the buds as well as the open blooms are valuable for cutting.

The illustration which is a part of this specification shows several partially opened buds and some open blooms at a stage of development obtained by cutting the blooms late one afternoon as the petals were unfolding and placing them in water for approximately a day. When the flowers have reached this stage, either indoors or out, the colors do not fade either in the sun or otherwise, but, to the contrary, they become more intense in color as the petals unfurl. This color characteristic is also one of the very important attributes of this new variety.

Following is a more detailed description of my new variety. Color references indicate Ridgeway's Color Standards and Nomenclature.

*The plant*

Growth habits: Vigorous climber, sending up stout canes some of which attain a length of more than eight feet. The plant covers approximately an equal width.

Blooming habit: Recurrent and continuous. This habit is commonly referred to in the nursery trade and by amateur rose growers as being "everblooming" and hence the term "everblooming climber" may properly be applied to this new and distinct variety. The first blooms appear in June at the same time older and once-blooming climbers are in flower. Then successive crops are produced right on during the seasons through October. Many blooms are produced at one time, therefore giving the mass color effect for which older climbing varieties are so well noted.

Hardiness: Withstands cold winters in the latitude of New York city and even farther north. It freezes back only slightly from the tips and in this respect is just as hardy as older varieties like Dr. Van Fleet and Mary Wallace.

Disease resistance: Very resistant to diseases common to roses, having inherited the well known disease resistant qualities of the Wichurainana Rose strain.

Foliage: Five to seven leaflets. Profuse and of splendid texture. Dark Forest Green (Plate XVIII). Terminal leaflet is usually about 1½ inches long by 1 inch wide; lateral leaflets are slightly smaller.

Stems: Strong and upright. Parrot (Plate VI).

*Peduncles or flower stems.*—Unusually long for a climbing rose. The green is overlaid with Pompeian Red (Plate XIII) on flower stems, and Brick Red (Plate XIII) on bud stems.

*Thorns.*—Sharp; slightly downward pointing; Pompeian Red (Plate XIII).

*The flower*

Bud:

*Shape.*—Ovoid.

*Size.*—Large. Average length ¾ inch when color first shows.

*Color.*—Opening buds are Coral Red to Jasper Red (Plate XIII) blending into Empire Yellow (Plate IV) at the base. As the buds unfurl they become Light Coral Red to Light Jasper Red (Plate XIII).

*Sepals.*—Simple; reflex early; approximately Parrot Green (Plate VI) on the outer surface and Dark Greenish Glaucous (Plate XLI) on the under surface.

Bloom:

*Size.*—Very large for a climbing rose, averaging 3½ inches in diameter when produced on terminal shoots and 2½ inches when produced on lateral shoots.

*Pettallage.*—Very double, having 55 to 65 petals.

*Borne.*—Some blooms are borne in large clusters on stout stems, while others are borne singly.

*Form.*—High centered but opening into cup-shape when older. Freshly opened bloom shows a rosette formation in the center consisting of 40 to 50 small petals which average approximately $\frac{3}{16}$ inch wide by ¼ inch long.

*Color.*—Newly opened flowers—petal backs, Light Jasper Red and Jasper Pink (Plate XIII); petal faces, tones of Flesh Color and Salmon Color, merging to Pale Flesh Color, Pale Salmon Color and Seashell Pink (all on Plate XIII). Flowers a day or two after opening—colors non-fading; same as freshly opened flowers but more intense.

*Textures.*—Very firm and substantial, making it long lasting both on the plant and as a cut flower.

*Size of outer petals.*—Average 1½ inches long and ¾ inch wide.

*Fragrance.*—Pleasing, spicy, and penetrating in all stages of bloom development, becoming more pronounced in the later stages.

Having thus disclosed my invention, I claim:

The new and distinct variety of climbing rose plant, substantially as herein described and illustrated, characterized particularly by its disease resistance; its hardiness; its vigorous growth; its everblooming and free-blooming habits; and its large, well-formed, long-lasting flowers having distinctive coloring ranging from Flesh Color to Jasper Red as indicated, and penetrating spicy fragrance which increases as the flower development advances.

MARTIN R. JACOBUS.